United States Patent [19]

Nicholas

[11] 4,378,476
[45] * Mar. 29, 1983

[54] PRESSURE OPERATED ELECTRIC SWITCH AND ALARM SYSTEM USING SUCH SWITCH

[76] Inventor: Noel Nicholas, 6, Verona Villas, O'Connell Ave., Limerick, Ireland

[*] Notice: The portion of the term of this patent subsequent to Apr. 21, 1998, has been disclaimed.

[21] Appl. No.: 217,607

[22] Filed: Dec. 18, 1980

Related U.S. Application Data

[63] Continuation-in-part of Ser. No. 907,461, May 19, 1978, Pat. No. 4,263,586, which is a continuation-in-part of Ser. No. 826,957, Aug. 22, 1977, abandoned.

[30] Foreign Application Priority Data

Aug. 20, 1976 [IE] Ireland .................................. 1867/76

[51] Int. Cl.³ .............................................. H01H 3/02
[52] U.S. Cl. ................................ 200/85 R; 200/86 R; 340/665; 340/666
[58] Field of Search .............. 340/568, 573, 576, 665, 340/666; 307/116, 119; 200/61.7, 85 R, 86 R, 86 A, 153 T, 329, 330–333

[56] References Cited

U.S. PATENT DOCUMENTS

| | | | |
|---|---|---|---|
| 1,758,546 | 5/1930 | Wartmann . | |
| 2,260,715 | 10/1941 | Ketchem | 200/85 R |
| 2,436,898 | 3/1948 | Rickmeyer | 200/159 |
| 2,458,192 | 1/1949 | Niles | 340/568 |
| 2,463,980 | 3/1949 | Lee | 200/85 A |
| 2,713,645 | 7/1955 | Lerch | 307/119 |
| 2,818,477 | 12/1957 | Gollhofer | 200/83 R |
| 3,273,038 | 9/1966 | Miller | 307/119 |
| 3,591,739 | 7/1971 | Kenton | 200/52 |
| 3,656,141 | 4/1972 | Hill | 340/272 |
| 3,824,536 | 7/1974 | Cherico | 340/52 R |
| 3,845,261 | 10/1974 | Blinkilde | 200/85 A |
| 3,852,736 | 12/1974 | Cook | 340/279 |
| 3,961,201 | 6/1976 | Rosenthal | 307/116 |
| 4,164,637 | 8/1979 | Miyazi | 200/86 R |
| 4,263,586 | 4/1981 | Nicholas | 340/568 |

FOREIGN PATENT DOCUMENTS

| | | |
|---|---|---|
| 438600 | 12/1926 | Fed. Rep. of Germany . |
| 2440029 | 3/1976 | Fed. Rep. of Germany . |
| 491879 | 6/1919 | France . |
| 420071 | 11/1934 | United Kingdom . |
| 1082411 | 9/1967 | United Kingdom . |
| 1145514 | 3/1969 | United Kingdom . |
| 1233467 | 5/1971 | United Kingdom . |
| 1308751 | 3/1973 | United Kingdom . |

*Primary Examiner*—G. P. Tolin
*Attorney, Agent, or Firm*—Sughrue, Mion, Zinn, Macpeak and Seas

[57] ABSTRACT

A pressure operated electrical switch and an alarm system for use in hospitals and nursing homes is constructed such that a force is applied to the upper surface of a leaf spring therein. Once the load is reduced below a predetermined value the leaf spring will move to close/open a microswitch or electrical contact means. The normal force applied to the leaf spring is the load on the leg of the hospital bed when occupied. If the bed occupant gets out of the bed the load on the leaf spring is reduced below a predetermined value and the consequent movement of the leaf spring opens/closes the switch means to actuate the alarm.

6 Claims, 9 Drawing Figures

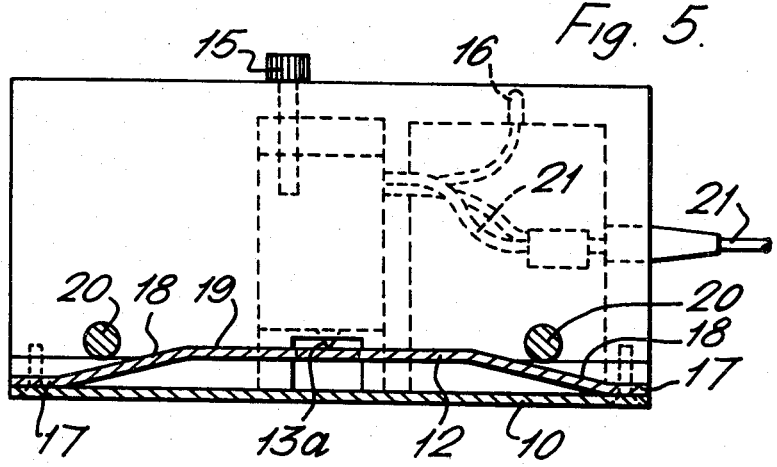
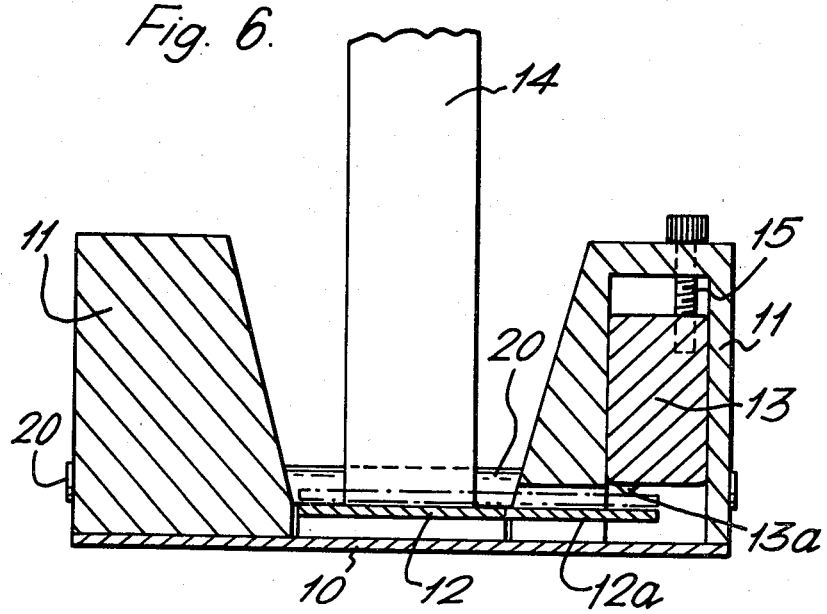

PRESSURE OPERATED ELECTRIC SWITCH AND ALARM SYSTEM USING SUCH SWITCH

CROSS REFERENCES TO RELATED APPLICATIONS

This application is a continuation-in-part of application Ser. No. 907,461, now U.S. Pat. No. 4,263,586 for "Pressure Operated Electric Switch and Alarm System Using Such Switch", filed May 19, 1978, now U.S. Pat. No. 4,263,586, which is a continuation-in-part of application Ser. No. 826,957, for "Pressure Operated Electric Switch and Alarm System Using Such Switch", filed Aug. 22, 1977, now abandoned.

BACKGROUND OF THE INVENTION

The present invention relates to a pressure operated electric switch and an alarm system using the switch.

SUMMARY OF THE INVENTION

The switch in accordance with the present invention is provided to give an alarm to a nurse or other person minding a patient when the patient gets out of the bed. The switch is placed under a leg of the bed and is adjusted such that when the bed is occupied by the patient, the pressure acting on the switch is sufficient to maintain the switch contacts in, for example, the open position, whereas when the bed becomes unoccupied, the switch contacts move to the closed position to give an alarm. The alarm may be audible and/or visible, and it may comprise a bell and/or a light.

The switch is constructed such that a force is applied to a pressure plate in the switch, and once the load is reduced below a predetermined value, the pressure plate will move under spring influence to close or open a microswitch by electrical contact means. The normal force applied to the pressure plate is the load on the leg of the hospital bed when occupied. If the bed occupant gets out of the bed, the load on the pressure plate is reduced below a predetermined value, and the subsequent movement of the pressure plate opens or closes the switch means to actuate the alarm.

In accordance with a preferred embodiment of the present invention, the pressure plate is in the form of a leaf spring, and is generally configured in a smooth "m" shaped form. The pressure plate/leaf spring thereby provides a stable support for the bed leg resting thereon, at the middle of the "m" shaped pressure plate.

BRIEF DESCRIPTION OF THE DRAWINGS

Particular embodiments of the pressure operated electric switches and alarm systems incorporating switches, are hereinafter described with reference to the accompanying drawings, in which:

FIG. 5 is a transverse vertical sectional view of the switch of FIG. 3;

FIG. 6 is a longitudinal vertical sectional view of the switch of FIG. 3;

DESCRIPTION OF THE PREFERRED EMBODIMENTS

Figure 1:
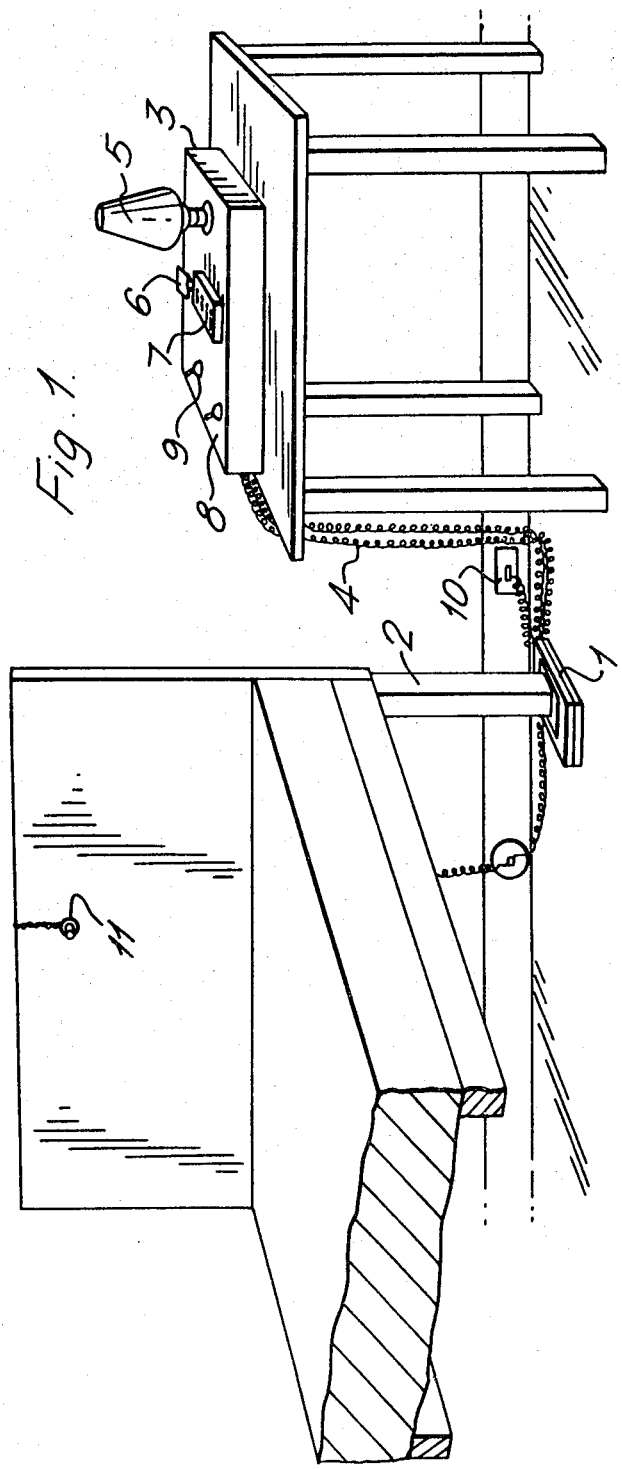
FIG. 1 is a schematic diagram of a switch and alarm circuit as installed in use so as to be actuated by the leg of a bed.

As shown in FIG. 1, a pressure-operated electric switch 1 is positioned below the end of a bed leg 2 and is connected to an alarm circuit 3 by pairs of wires 4.

Figure 2:
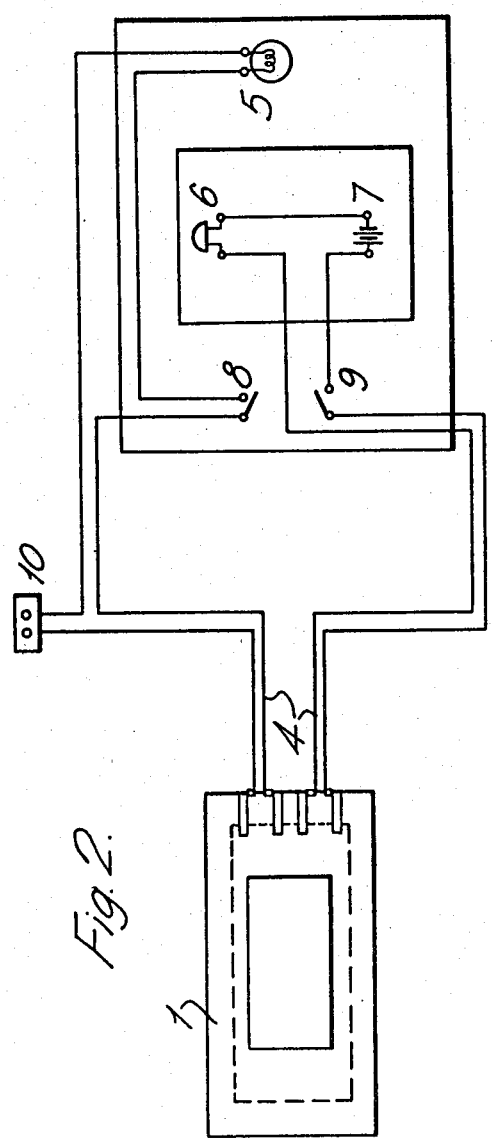
FIG. 2 is a circuit diagram of the switch and alarm circuit of FIG. 1.
Figure 3:
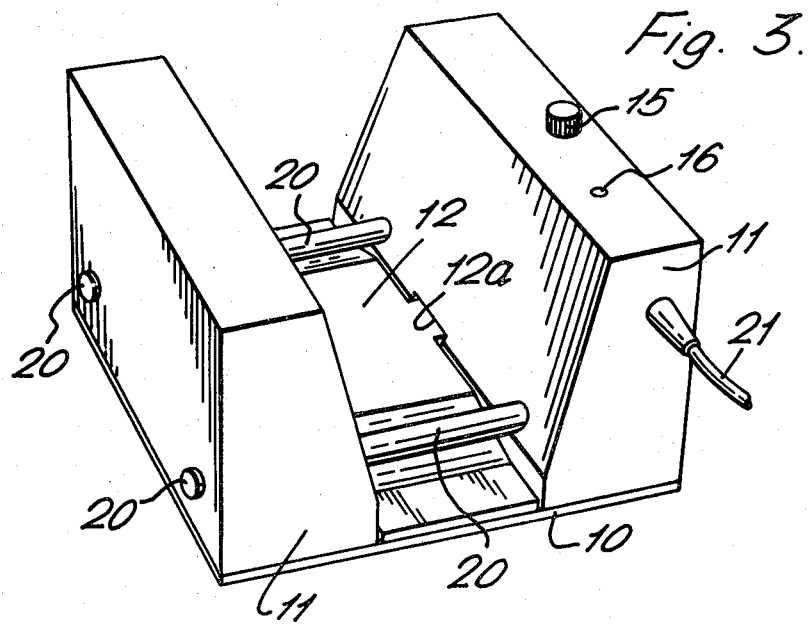
FIG. 3 is a perspective view of a first embodiment of the switch in accordance with the present invention.
Figure 4:
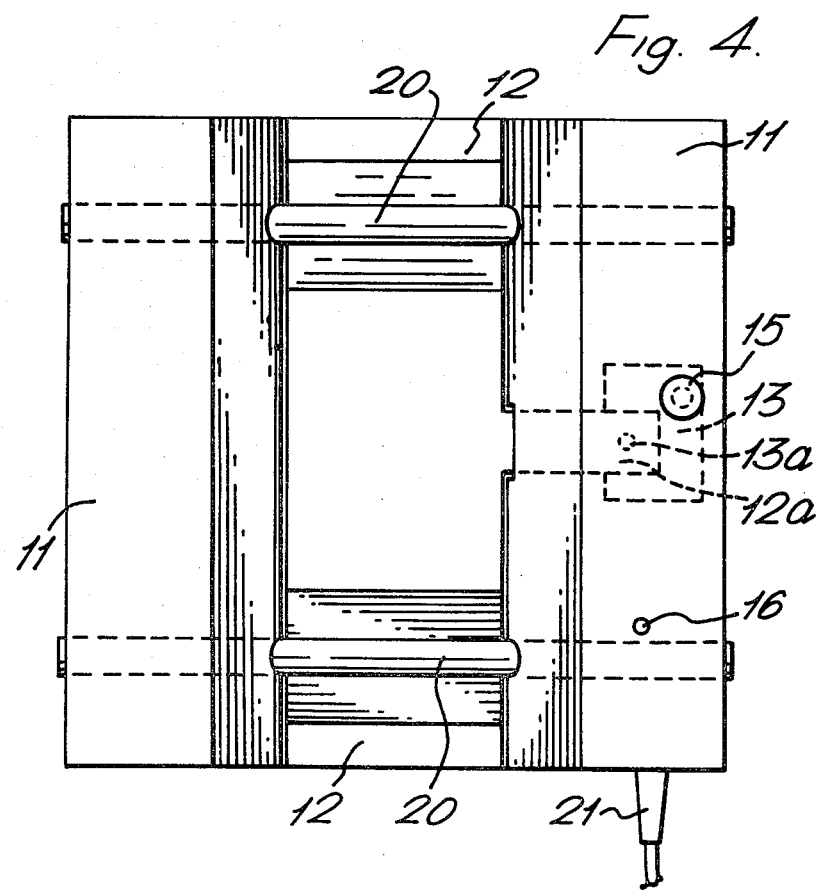
FIG. 4 is a plan view of the switch of FIG. 3.

The alarm circuit 3 includes a light 5, a bell 6, a battery 7 for energizing the bell circuit, a switch 8 in the light circuit and a switch 9 in the bell circuit, a switch 8 in the light circuit and a switch 9 in the bell circuit. The light circuit is energized from a main supply socket outlet 10. Normally, the switches 8, 9 are in the closed position but may be opened to interrupt the alarm. A push button switch 11 for use with the main house call bell is provided mounted on the bedhead. The circuit diagram of the alarm circuit is shown in FIG. 2.

The present invention is directed to a pressure operated electrical switch which accommodates a leaf spring centrally mounted on a base and adapted under the influence of a load such as that exerted by a bed leg for vertical movement relative to the base. The leaf spring acts not only as a spring but also as a pressure plate upon which the bed leg rests. A small strip of metal which is operatively connected to the leaf spring acts as a level indicator and the strip of metal co-operates with a microswitch to provide the alarm.

This embodiment is particularly adapted to accommodate a castor wheel, i.e., a wheel at the bottom of a bed leg, by having the leaf spring/pressure plate openly centrally mounted on the base and walled in on its two sides by the switch casing which houses the switch mechanism which responds to the movement of the level indicator attached to the leaf spring. In this manner the caster wheel is positively located in a guideway formed by said walls formed by the casing and the leaf spring mounted within the guideway so formed acts not only as the spring means and pressure plate of the invention but also as a locating ramp for the caster wheel.

The switch of FIGS. 3-6 comprises a molded plastic housing including a base 10 and side walls 11. A steel pressure plate 12 is mounted on the base 10 with the pressure plate 12 being a suitably shaped leaf spring adapted for vertical flexing movement relative to the base 10. One of the side walls 11 locates and accommodates a switch mechanism 13 which co-operates with the pressure plate 12 to open/close an electric circuit to deactuate/actuate an alarm system.

The vertical flexing movement of the pressure plate 12 relative to the base 10 is determined by the force exerted upon the exposed face of the central portion of plates 12 such as by a wheel 14 of a hospital bed. If a patient is in the bed the force on the plate 12 holds a tongue 12a of the plate 12 out of contact with a switch 13. If the patient leaves the bed, the resultant reduction in weight and hence the force on the plate 12 allows the plate 12 to flex upwardly with the tongue 12a engaging the contact 13a of the switch 13 to close an electric circuit and actuate an audible and/or visual alarm.

The vertical position of the switch 13 within the respective side wall 11 of the housing is adjustable by means of an adjustment screw 15. Since the leaf spring pressure plate 12 cannot be varied at will adjustment of the switch position allows the device to cater for varying weights of patients in a bed.

A visual indicator means is provided comprising a light 16 operatively connected to the switch 13. In use the light 16 operates when the switch 13 is closed. Accordingly, a nurse setting the alarm adjusts the switch position—with the patient in the bed—until the light goes out. This means the switch contact 13a and the plate tongue 12a are just separated and the device correctly set. The light 16 also serves to confirm to the nurse—as she sets the device—that it is operative. If no light shows then the device may be defective.

The leaf spring pressure plate 12 has its side edges 17 in firm contact with the base 10 and it is inclined as at 18 to a flat plateau 19. The inclined portions 18 serve not only to permit the pressure plate 12 to function as a leaf spring but to also form ramps for rolling the hospital bed wheel 14 on the flat central portion or plateau 19. The side walls 11 are bridged by steel rods 20 which hold the leaf spring pressure plate 12 loosely in position. The steel rods 20 allow adequate vertical movement of the plate 12. The steel rods 20 also act primarily to hold the bed wheel 14 in position in contact with the plateau portion 19 of the leaf spring pressure plate 12.

Figure 7:
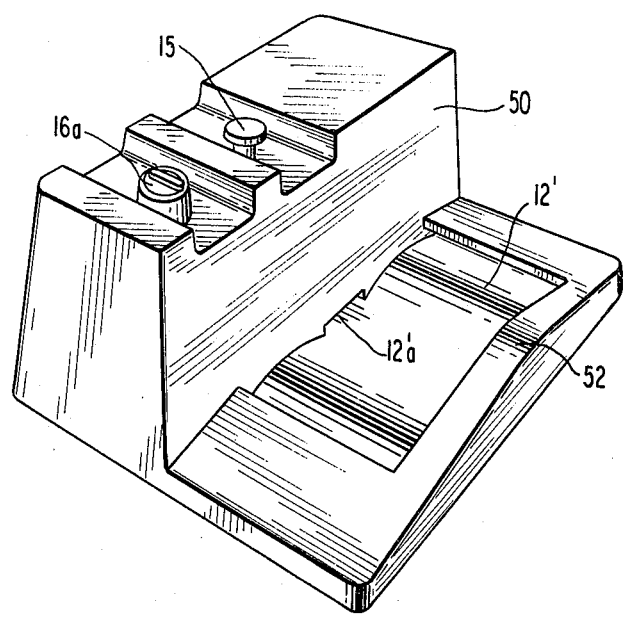
FIG. 7 is a perspective view of a preferred second embodiment of the switch in accordance with the present invention.
Figure 8:
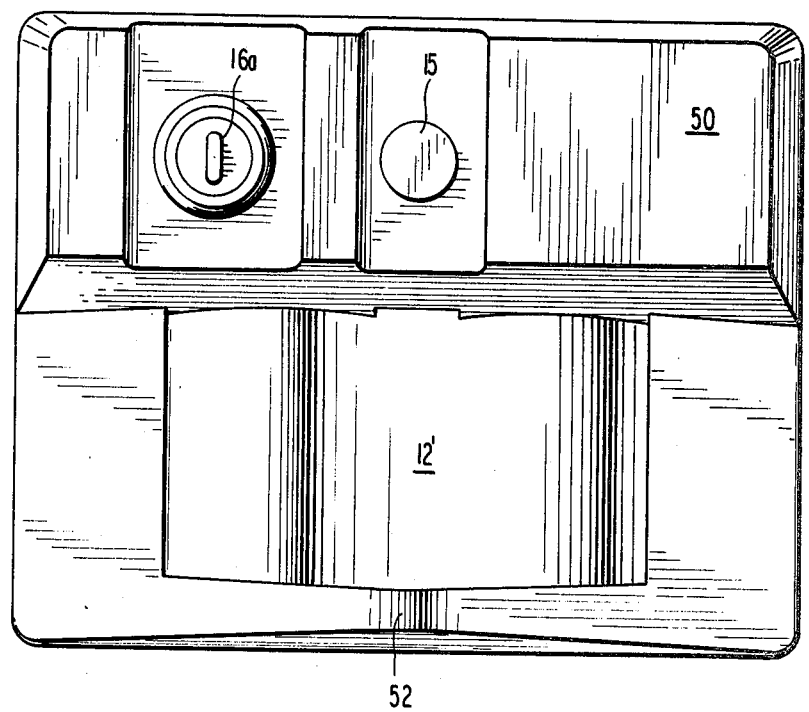
FIG. 8 is a plan view from above of the switch shown in FIG. 7.
Figure 9:
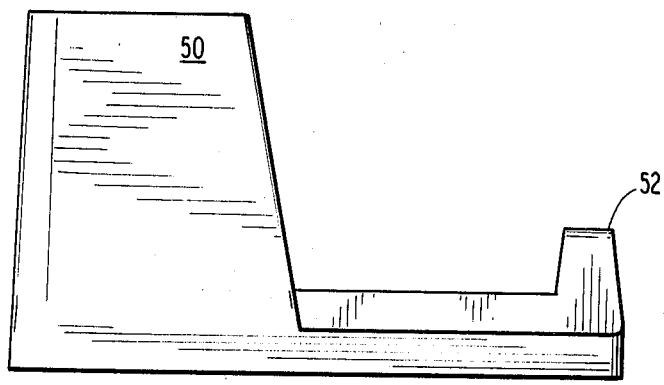
FIG. 9 is a side plan view of the switch shown in FIG. 7.

The second and preferred embodiment of the switch in accordance with the present invention is illustrated in FIGS. 7 through 9, and is substantially the same as the first embodiment of the switch in accordance with the present invention except for the configuration of the leaf spring 12' and side walls 50 and 52. More specifically, the leaf spring 12' is contoured in a smooth "m" shape so as to form a vertical depression across the tongue 12a' of the plate to thereby automatically locate the bed leg in the depressed region. Furthermore, the side wall 50, embodying the switching mechanism (generally shown in the right hand wall of FIG. 6), is vertically higher than the opposing wall 52. Thus, the embodiment of the switch illustrated in FIGS. 7 through 9 provides easier and more rapid deployment of the bed leg on the switch as opposed to the switch embodiment of FIGS. 3 through 6. On-off switch 16a is provided at the top of the side wall 50, along with adjustment screw 15.

It will be readily appreciated that the alarm system of the present ivention has particular application in hospitals and nursing homes. In such use it is desirable and technically feasible using known electrical components to integrate the alarm system of the present invention with existing nurse calling systems.

I claim:

1. A pressure-operated electric switch for use in conjunction with a hospital bed and adapted for insertion under one leg of the bed to signal the absence of a patient therein, the electric switch comprising a portable housing having a base, a horizontally disposed leaf spring mounted in the housing for vertical movement relative to the base, the leaf spring having an upper surface and a spring portion extending upwardly from a supporting surface in the housing below the upper surface and biasing the upper surface upwards, the housing having an aperture exposing at least a portion of the upper surface of the leaf spring to allow the application of an external force to the upper surface in opposition to the spring portion, means for centrally locating the lower end of a leg of a bed in overlying relationship to said upper surface, switch means mounted inside the housing and adapted for actuation by movement of the upper surface, the switch means being actuated at a selected height of the upper surface above the base, and means to adjust the height of the upper surface at which the switch means is actuated, wherein the means for centrally locating comprises a vertical depression in a portion of the upper surface of the leaf spring.

2. A switch as claimed in claim 1 wherein said vertical depression is centrally located on the upper surface of the leaf spring.

3. A switch as claimed in claim 2 wherein a leg of a bed is disposed within the vertical depression.

4. A switch as claimed in claim 3 wherein the upper surface of the leaf spring is substantially shaped like a smooth "m".

5. A switch as claimed in one of claims 1, 2, 3, or 4 wherein the locating means further comprises a pair of upstanding side walls of the housing defining therebetween a passage way, the leaf spring extending along the length of the passage way.

6. The switch as claimed in claim 5 wherein said pair of upstanding side walls comprise a first side wall and a second side wall, the second side wall being vertically shorter than said first side wall.

* * * * *